(12) United States Patent
Bloch et al.

(10) Patent No.: US 6,728,642 B2
(45) Date of Patent: Apr. 27, 2004

(54) METHOD OF NON-LINEAR ANALYSIS OF BIOLOGICAL SEQUENCE DATA

(75) Inventors: Karen Marie Bloch, Wilmington, DE (US); Gonzalo Ramiro Arce, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 106 days.

(21) Appl. No.: 10/108,841

(22) Filed: Mar. 27, 2002

(65) Prior Publication Data

US 2003/0097227 A1 May 22, 2003

Related U.S. Application Data

(60) Provisional application No. 60/279,572, filed on Mar. 29, 2001.

(51) Int. Cl.[7] .......................... G06F 19/00; G01N 33/48
(52) U.S. Cl. .............................. 702/20; 702/27; 702/30
(58) Field of Search ............................... 702/20, 27, 30

(56) References Cited

FOREIGN PATENT DOCUMENTS

WO     WO 0067200     11/2000

OTHER PUBLICATIONS

Cosic, Irena. Macromolecular Bioactivity: Is It Resonant Interaction Between Macromolecules?—Theory and Applications. Dec. 1994, vol. 41 IEEE Transactions on Biomedical/Eng.

Tomii & Kaneshia. Analysis of amino acid indices and mutation matrices for sequence comparison and structure prediction of proteins. Oxford University Press. Protein Engineering, 1996. vol. 9 pp. 27–36.

Veljkovic, V. et al. Is It Possible to Analyze DNA and Protein Sequences by the Methods of Digital Signal Processing?1985, IEEE Transactions on Biomedical Engineering vol. BME–32 pp. 337–341.

Eisen et al. Cluster analysis and display of genome–wide expression patterns. 1998. Proceedings of The National Academy of Sciences. vol. 95 pp. 14863–14868.

Arce, Gonzalo. Elimination of Interference Terms of the Discrete Wigner Distribution Using Nonlinear Filtering, IEEE Transactions on Signal Processing vol. 48 Aug. 2000 . pp. 2321–2326.

Kawashima et al. AAindex: Amino Acid Index Database. Nucleic Acids Research, 1999, vol. 27, No. 1.

D'Haeseleer et al. Mining the Gene Expression Matrix: Inferring Gene Relationships From Large Scale Gene Expression Data. Information Processing in Cells and Tissues, pp. 203–212, 1998. Plenum Publishing.

Fang and Cosic. Protein Structure Analysis using the Resonant Recognition Model and Wavelet Transforms. vol. 21, Nov. 4, 1998. Australasian Physical & Engineering Sciences in Medicine pp. 179–185.

*Primary Examiner*—John S. Brusca

(57) ABSTRACT

A method of classifying biological elements into functional families includes the steps of representing a characteristic numerically, performing a time-frequency transform on the numeric representation, and identifying biological elements of a common functional family by clusters of data having a common frequency characteristic in the time-frequency domain. Biologically active regions on those biological elements are identified by an amplitude analysis of the clusters.

17 Claims, 13 Drawing Sheets

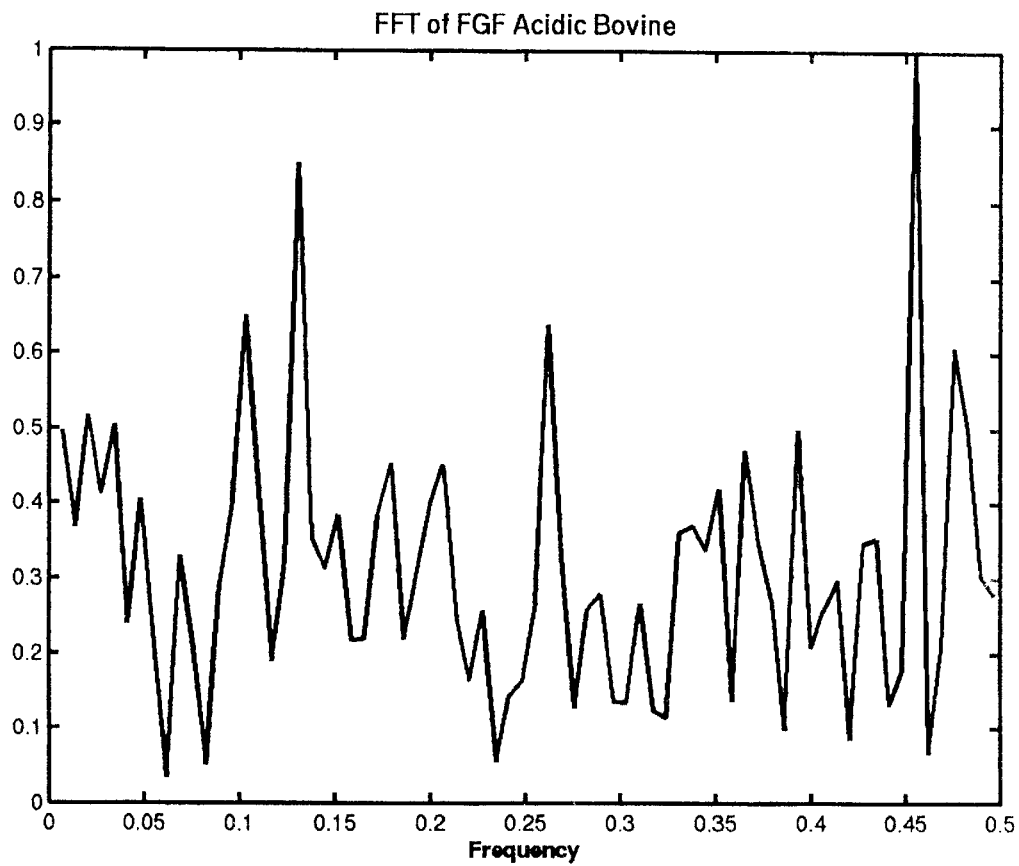
PRIOR ART    FIGURE 2A

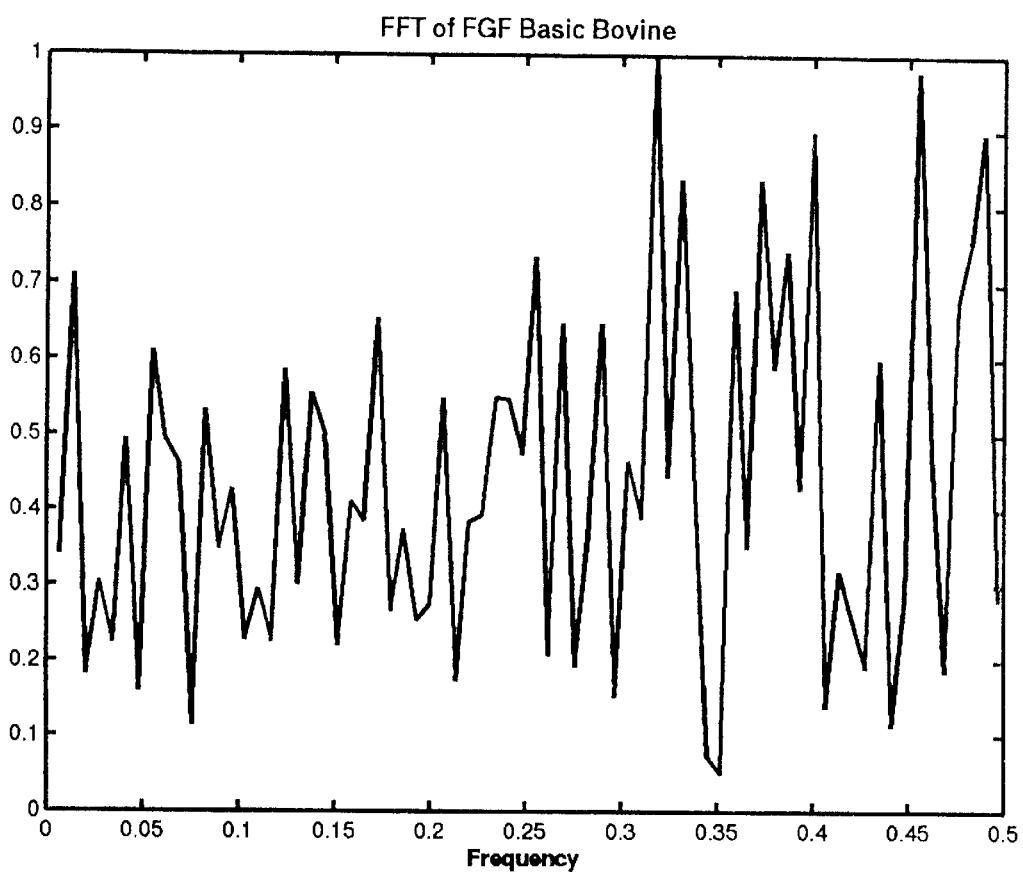
PRIOR ART    FIGURE 2B

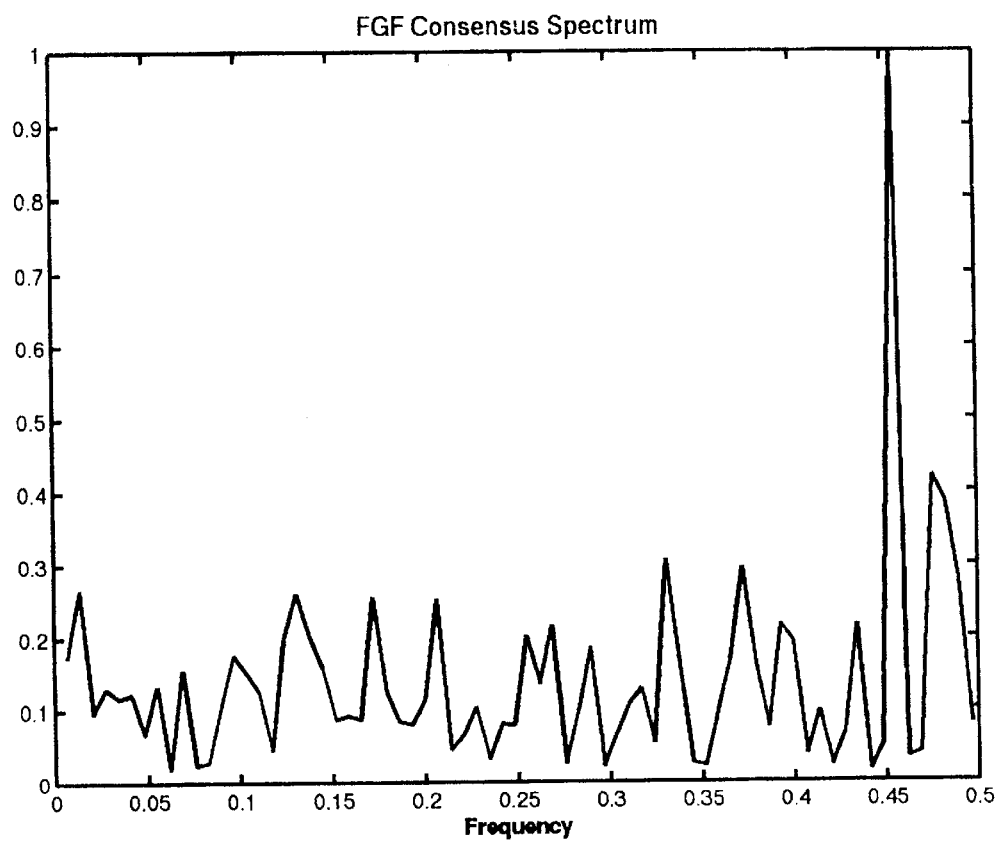
PRIOR ART                    FIGURE 3

METHOD OF NON-LINEAR ANALYSIS OF BIOLOGICAL SEQUENCE DATA

BACKGROUND OF THE INVENTION

1. Field of the Invention

The present invention relates to a method of classifying biological elements into functional families and identifying biologically active regions of the biological element.

2. Description of the Prior Art

Genomes carry all information of life from one generation to the next for every organism on earth. Each genome, which is a collection of DNA molecules, can be represented as a series of strings comprised of four letter symbols. Today, the genomes of a worm known as *C. elegans*, the fruit fly, the human and a weed known as Arabidopsis, as well as several dozen microbial genomes are available. Most of these data are accessible free of charge, encouraging the exploration of this data. However, it is not the genes, but the proteins they encode that actually perform the functions of living cells. A search for protein function requires that each protein and its structure be identified and characterized, and that every protein—protein interaction be characterized.

Classification of Proteins Proteins are the molecules constructed from linear sequences of smaller molecules called amino acids. There are twenty naturally occurring amino acids and they can be represented in a protein sequence as a string of alphabetic symbols. Protein molecules fold to form specific three dimensional shapes which specify their particular chemical function.

Analysis of protein sequences can provide insights into function and can also lead to knowledge regarding biologically active sites of the protein. While analysis of protein sequences is often performed directly on the symbolic representation of the amino acid sequence, patterns in the sequence are often too weak to be detected as patterns of symbols.

Alternative sequence analysis techniques can be performed by assigning numerical values to the amino acids in a protein. The numerical values are derived from the physico-chemical properties of the amino acid such as hydrophobicity, bulkiness, or electron-ion interaction potential (EIIP) and are relevant to structural folding or biological activity.

It has been recognized that proteins of a given family have a common characteristic frequency component related to their function which may be used to classify proteins into functional families.

Frequency Analysis Methods The Resonant Recognition Model is an attempt to use frequency analysis to determine the characteristic frequency components of a family of proteins.

The Resonant Recognition Model or RRM, is described by I. Cosic in "Macromolecular bioactivity: Is it resonant interaction between macromolecules?—theory and applications," *IEEE Transactions on Biomedical Engineering*, vol. 41, December 1994. The RRM is a physico-mathematical model that analyzes the interaction of a protein and its target using digital signal processing methods. One application of this model involves prediction of a protein's biological function. In this technique a Fourier transform is applied to a numerical representation of a protein sequence and a peak frequency is determined for a particular protein's function. The aim of this method is to determine a single parameter that correlates with a biological function of genetic sequences. To determine such a parameter it is necessary to find common characteristics of sequences with the same biological function. The cross-spectral function determines common frequency components of two signals. For a discrete series, the cross-spectral function is defined as:

$$S_n = X_n Y^*_n, \quad n=1,2,\ldots,N/2$$

where $X_n$ are the Discrete Fourier Transform (DFT) coefficients of the series $X(n)$ and $Y_n^*$ are the complex conjugate DFT coefficients of the series $Y(n)$. Peak frequencies in the cross-spectral function define common frequency components for analyzed sequences. The common frequency components for a group of protein sequences can be defined as follows:

$$|M_n| = |X1_n||X2_n| \ldots |XM_n|, \quad n=1,2,\ldots,N/2$$

This methodology can be illustrated via an example. Fibroblast growth factors (FGF) constitute a family of proteins that affect the growth, differentiation, and survival of certain cells. The symbolic representations of two FGF amino acid sequences are shown below:

```
>FGF basic bovine
PALPEDGGSGAFPPGHFKDPKRLYCKNGGFFLRIHPDGR  SEQ ID NO:1

VDGVREKSDPHIKLQLQAEERGVVSIKGVCANRYLAMKE

DGRLLASKCVTDECFFFERLESNNYNTYRSRKYSSWYVA

LKRTGQYKLGPKTGPGQKAILFLPMSAKS

>FGF acid bovine
PNLPLGNYKKPKLLYCSNGGYFLRILPDGTVDGTKDRSD  SEQ ID NO:2

QHIQLQLCAESIGEVYIKSTETGQFLAMDTDGLLYGSQT

PNEECLFLERLEENHYNTYISKKHAEKHWFVGLKKNGRS

KLGPRTHFGQKAILFLPLPVSSD
```

Symbolic representations, such as these, can be translated into numerical sequences using the EIIP index, described by K. Tomii and M. Kanehisa in "Analysis of amino acids and mutation matrices for sequence comparison and structure prediction of proteins," *Protein Engineering*, vol. 9, January 1996.

V. Veljkovic, I. Cosic, B. Dimitrjevic, and D. Lalovic, in "Is it possible to analyze DNA and protein sequences by the methods of digital signal processing?," *IEEE Transactions on Biomedical Engineering*, vol. 32, May 1985, have shown that the EIIP correlates with certain biological properties.

The graphical representation of the corresponding numerical sequences for the FGF proteins (SEQ ID NO:1 and SEQ ID NO:2) obtained by replacing every amino acid with its EIIP value can be see in FIGS. 1A and 1B. A DFT is performed on each numerical sequence. The resulting spectra are shown in FIGS. 2A and 2B. The cross-spectral function of the two FGF spectra generates the consensus spectrum shown in FIG. 3. For the spectrum plots the x-axis represents the RRM frequencies and the y-axis are the normalized intensities. The prominent peak denotes the common frequency component for this family of proteins.

The presence of a peak frequency in a consensus spectrum implies that all the analyzed sequences have one frequency component in common. This frequency is related to the biological function provided the following conditions are met:

one peak only exists for a group of protein sequences sharing the same biological function;

no significant peak exists for biologically unrelated protein sequences;

peak frequencies are different for different biological functions.

However, since frequency analysis alone contains no spatial information, there is no indication as to which residues contribute to the frequency components. The RRM technique lacks the ability to reliably identify the individual amino acids that contribute to that peak frequency.

Spatial Analysis Methods Frequency analysis alone cannot handle the transitory nature of non-stationary signals. However, a time-frequency representation (or space-frequency representation as is synonymously known in the art. See Leon Cohen, *Time-Frequency Analysis.* Prentice Hall, 1995. P. 113) of a signal provides information about how the spectral content of the signal evolves with time (or space) and therefore provides a tool to analyze non-stationary signals.

In an attempt to provide spatial information relating to the proteins Q. Fang and I. Cosic in "Prediction of active sites of fibroblast growth factors using continuous wavelet transforms and the resonant recognition model," *Proceedings of The Inaugural Conference of the Victorian Chapter of the IEEE EMBS,* 1999 describe a method using a continuous wavelet transform to analyze the EIIP representations of protein sequences. The continuous wavelet transform (CWT) is one of the time-frequency or space-frequency representations. Because the CWT provides the same time/space resolution for each scale the CWT can be chosen to localize individual events such as active site identification. The amino acids that comprise the active site(s) are identified as the set of local extrema of the coefficients in the wavelet transform domain. The energy concentrated local extrema are the locations of sharp variation points of the EIIP and are proposed by Fang and Cosic as the most critical locations for a protein's biological function.

Experiments have shown that the potential cell attachment sites of FGF's are between residues 46–48 and 88–90. FIG. 4 is a gray scale plot of a CWT spectrogram (a time-frequency representation) of the FGF protein (SEQ ID NO:1 and SEQ ID NO:2) of Example 1. This plot was produced using an intensity plot routine in MATLAB, available from MathWorks, Natick, Mass. The gray scale on this plot represents the amplitude of the data, the lightest gray being the highest amplitude and the black being the lowest amplitude. For clarity of illustration the background, which would otherwise be completely black, has been rendered white. It can be observed that there are two bright regions at the higher frequencies from scale 1.266 to scale 2.062, which correspond to the amino acids at the active sites. These regions are enclosed in white rectangular boxes and are labeled with the reference numerals 100 and 200, respectively.

While the wavelet transform technique shows promise for identifying amino acids at potential biologically active sites, it does not reveal the characteristic frequency component of the Resonant Recognition Model. The spectrogram of the CWT can often be difficult to interpret. It is the weaknesses of these prior art methods described above that are overcome by the present method.

Classification of Genes While the study of proteins leads to the understanding of the functions within organisms it is still necessary to understand how genes in organisms are regulated since it is this regulation which influences the production of the proteins under the correct environmental conditions. Within the last few years miniaturized laboratory analysis technology using substrates containing an array of samples has become available. These sample arrays are commonly known as "microarrays" or "gene chips". Microarray technology is revolutionizing functional genomics research by allowing scientists to measure the expression level of thousands of genes simultaneously from a single experiment. The discovery of sets of genes with similar expression patterns has a variety of uses such as: finding genes that might be involved with a particular disease by comparing their patterns with genes that are known to be associated with the disease; characterizing the function of an unknown gene by comparing it to a class of genes of a known class; and finding genes with similar patterns of behavior over time.

Linear Classification Methods However, a standard protocol for microarray data analysis has not yet been established. Many data mining techniques are currently in use for microarray data analysis. Eisen, et.al. in "Cluster analysis and display of genome-wide expression patterns", *Proceedings of the National Academy of Science,* Vol. 95, pp. 14863–14868, show that standard linear correlation coefficients can be calculated for gene pairs. This information can then be passed to a hierarchical clustering software package to visualize relationships amongst the genes. Eisen's data set contains over six thousand genes and can be found at http://rana.stanford.edu/clustering.

For simplicity of illustration of Eisen's method, a randomly selected subset of the yeast genes from four functional families of Eisen's data set was selected. This subset was clustered using Eisen's standard correlation coefficients and the results passed to the hierarchical clustering algorithm known as "PHYLIP" (Phylogeny Inference Package), version 3.57c (1995), distributed by the author, Joseph Fellsenstein, at http://evolution.genetics.washington.edu/phylip.html.

FIG. 10 illustrates the results of this prior art technique. As may be appreciated from FIG. 10 the functional families "Glycolysis" and "Protein Degradation" do not form tight clusters. In fact, these functional families are somewhat disjoint. This deficiency is attributed to the use of a linear correlation metric on what is inherently a nonlinear relationship of the gene expression and the functional families.

In view of the foregoing it is believed advantageous to use a nonlinear time-frequency transform to identify the frequency components that classify biological elements into functional families, while simultaneously retaining spatial information involving secondary structure and biologically active sites.

Definition of Terms

The relative terms "biological element: biological subelement" as used herein are meant to express biological entities related in next-adjacency in a hierarchy, with the "biological element" occupying the higher level in the hierarchy with respect to the "biological subelement".

For example, in a first hierarchy:

protein sequence
  amino acid
    dna sequence
      nucleotide the first member of the following hierarchically adjacent pairs of entities is the biological element while the second member of the pair is the biological subelement, thus:

protein sequences:amino acid amino acid:dna sequences dna sequences:nucleotide.

As a further example, in a second hierarchy:

gene expression experiment gene gene expression value a "gene expression value" is a biological subelement of a "gene" (the biological element) in expression experiments across genes. A "gene" can be a biological subelement of a "gene expression experiment" (the biological element). A gene expression value, for example, might be a physico-chemical property measurement of an amino acid.

The term "functional family" refers to biological elements exhibiting similar behaviors under the same environmental conditions. The term includes:

Proteins with a common biological function;

DNA sequences with common regions;

Genes with related expression behavior; and

Cell line similarity based on gene expression.

SUMMARY OF THE INVENTION

The present invention is a method of classifying a biological element comprised of biological subelements into a functional family, wherein each family is represented by a cluster of data points around a common frequency characteristic of a time-frequency transform, the method comprising the steps of:

a) converting a symbolic representation of a sequence of biological subelements to a numeric representation of that sequence;

b) performing a time-frequency transform on the numeric representation;

c) identifying a cluster of data having a common frequency characteristic in the time-frequency domain, thereby to identify a biological element in the functional family corresponding to that cluster.

The present invention may be implemented to classify a protein into a functional family, wherein each family is represented by a cluster of data points around a common frequency characteristic of a time-frequency transform, the method comprising the steps of:

a) converting a symbolic representation of a primary amino acid sequence data to a numeric representation of that sequence;

b) performing a time-frequency transform on the numeric representation; and c) identifying clusters of data having a common frequency characteristic in the time-frequency domain, thereby to identify proteins of a common functional family.

The resulting transformed data may be plotted in the time-frequency domain using commercially available plotting routines.

The preferred time-frequency transform is the Wigner-Ville time-frequency transform. Since this transform is quadratic in nature, cross-terms representing unwanted interference are produced. Accordingly, the method may further include the step of filtering the interference terms from the transformed data. The preferred filter method is the center affine filter method.

In general, each numeric representation may be either a scalar representation of a characteristic of each biological subelement or a vector representation of multiple characteristics of each biological subelement. The vector representation may be reduced to a minimal set of dimensions which preserves the functionally important features of the biological element.

When classifying a biological element each numeric representation may be either a scalar representation of a physico-chemical property of each biological subelement or a vector representation of multiple physico-chemical properties or each biological subelement. The vector representation may be reduced to a minimal set of dimensions which preserves the functionally important features of the biological element.

Biologically active regions are identified by relatively high amplitude clusters of data points. Accordingly, the method may further include the step of identifying clusters of data points whose amplitude exceeds a predetermined threshold, thereby to identify biologically active regions in the biological element.

BRIEF DESCRIPTION OF THE DRAWINGS

The invention will be more fully understood from the following detailed description, taken in connection with the accompanying drawings and the accompanying sequence descriptions, which form a part of this application and in which:

FIGS. 2A and 2B show prior art Fast Fourier Transform (FFT) representations of the FGF proteins;

FIG. 3 shows a prior art consensus spectrum of bovine FGF proteins;

The gray scale plots FIGS. 4, 6, 7, 8 and 9 are produced using intensity plot routines in MATLAB, available from MathWorks, Natick, Mass. The gray scale on each plot represents the amplitude of the data, the lightest gray being the highest amplitude and the black being the lowest amplitude. For clarity of illustration the background, which would otherwise be completely black has been rendered white. An equivalent three-dimensional perspective plot or color intensity plot of each of these figures may be obtained by utilizing the capabilities available in the MATLAB package referenced above.

Figure 1A:
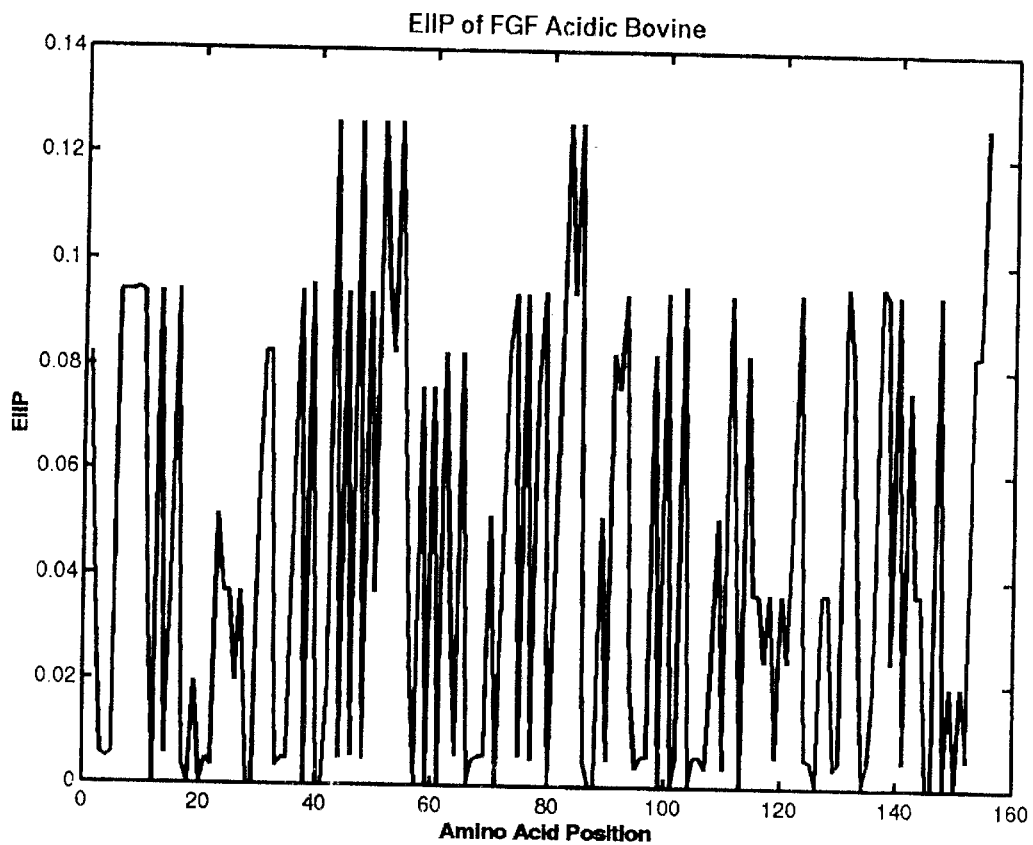
FIGS. 1A and 1B show prior art numerical EIIP representations of the FGF Proteins.
Figure 1B:
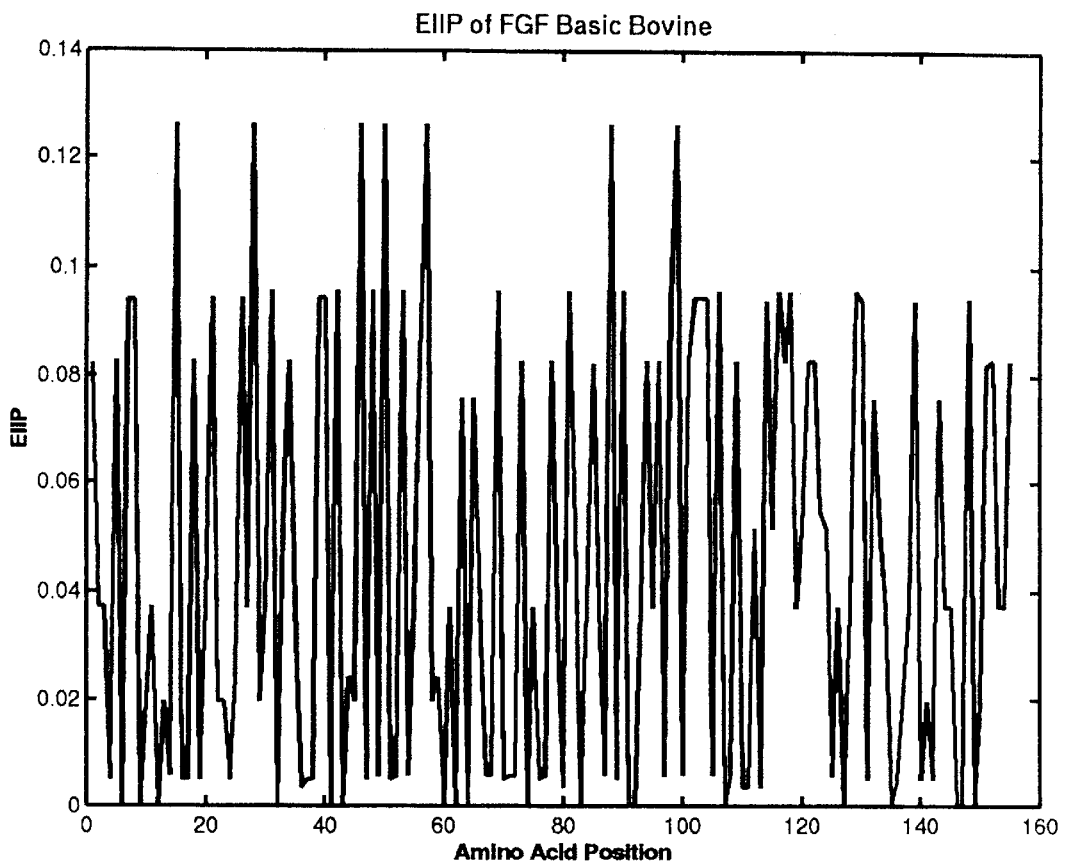
Figure 4:
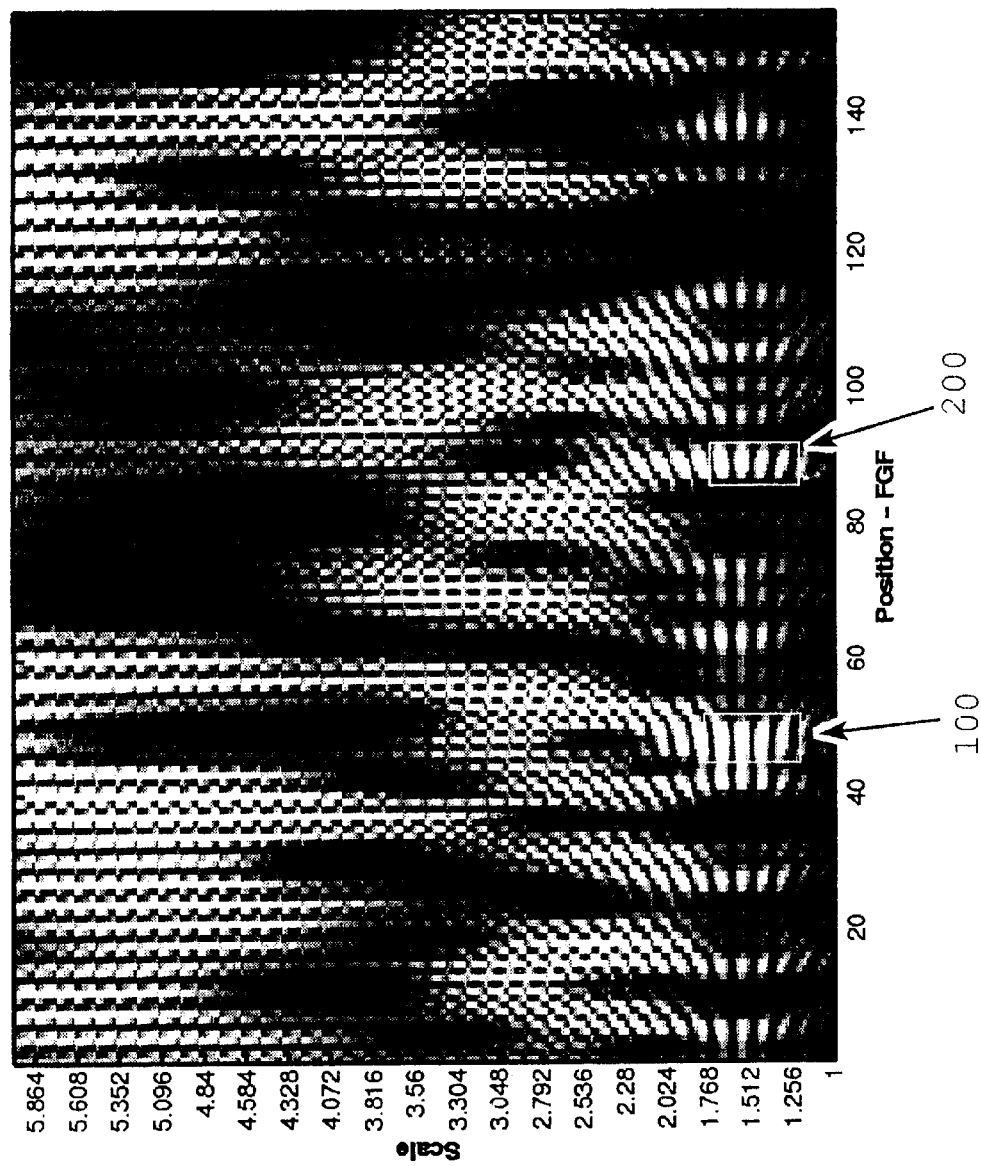
FIG. 4 shows a gray scale intensity plot of a continuous wavelet spectrogram of FGF protein.

The accompanying sequence descriptions appended after the Abstract comply with 37 C.F.R. 1.821–1.825

("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NO:1 is an amino acid sequence known as FGF basic bovine.

SEQ ID NO:2 is an amino acid sequence known as FGF acid bovine.

DETAILED DESCRIPTION OF THE INVENTION

Throughout the following detailed description similar reference characters refer to similar elements in all Figures of the drawings. The use of the present invention for classifying a biological element comprised of biological subelements into functional families is described in the context of the classification of a protein (the biological element) formed of amino acids (the biological subelements) into a functional family. Biologically active regions of the biological element may be subsequently determined by identifying clusters of data points whose amplitude exceeds a predetermined threshold.

Figure 5:
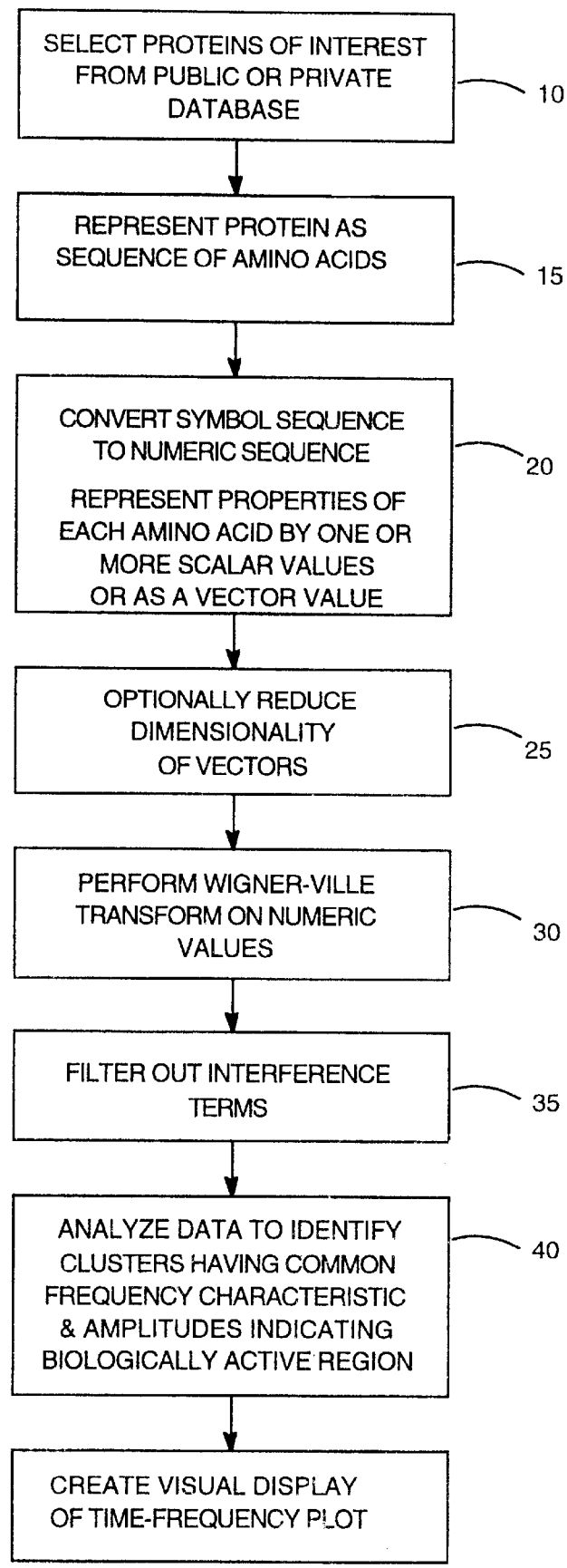
FIG. 5 is a block diagram of the method of the present invention.

As indicated in FIG. 5 by reference numerals 10 and 15, as a preliminary step a protein of interest is selected from a public or private database. The protein is symbolically represented alphabetically as a sequence of amino acids. For example, the first five symbols of the protein FGF basic bovine are:

{PALPE ... }

The symbol " . . . " indicates that additional amino acids and/or additional properties may be present in the scalar or vector representations.

The first step in accordance with the method of the present invention (as indicated by the reference numeral 20 in FIG. 5) is the conversion of the symbolic representation of the protein to a numeric representation where each amino acid is represented by one or more numeric values which represent physico-chemical/biochemical properties. The numeric representation may take the form of either a scalar value or a vector. Thus, for the symbolic representation of an amino acid sequence:

P A L P E . . . , the corresponding single-value scalar numeric representation may be:

1.95 0.61 1.53 1.95 0.47 . . . .

Alternatively the symbolic representation of the protein may be converted to a vector numeric representation for each amino acid where each column is a single amino acid and each row is a different measurement of that amino acid's properties.

Thus, for the same symbolic representation:

P A L P E . . . , the corresponding vector representation may be:

| 1.95 | 0.61 | 1.53 | 1.95 | 0.47 | ... |
| -2.50 | 0.96 | 0.92 | -2.95 | 0.53 | ... |
| 0.97 | 0.37 | 0.53 | 0.97 | 0.53 | ... |

As suggested by the reference numeral 25 in FIG. 5 the dimensionality of data vectors may be optionally reduced to a minimal set of dimensions which preserves the functionally important features of the protein. This reduction is especially useful when dealing with a large database of indices. This reduction in dimensionality can be accomplished, for example, using analysis routines such as principal component analysis (PCA), independent component analysis (ICA), or partial least squares or the technique described in Published PCT Application WO 00/67200 (published Nov. 9, 2000).

As indicated by the reference numeral 30 in FIG. 5 the next step in the present method is to perform a time-frequency transform on the numeric representation of each amino acid. This numeric representation can be considered a non-stationary signal. Time-frequency or time-scale representations are often used for the analysis of non-stationary signals. Since the numeric representation of amino acids is considered to be such a non-stationary signal the employment of a time-frequency transform is indicated.

Any time-frequency transform that provides a representation of a nonstationary signal in both the time(space) and the frequency domain may be used. Suitable time-frequency transforms to analyze the numeric representations of the amino acids include the Choi-Williams and the Wigner-Ville transforms. The Wigner-Ville transform, because it provides a quadratic time-frequency representation, provides good resolution in both the time (space) domain and the frequency domain, is preferred.

The Wigner-Ville transform, also known as the "Wigner-Ville Distribution" is described in: E. P. Wigner, "On the Quantum Correction for Thermodynamic Equilibrium", Phys. Rev., vol. 40, pp 749 (1932) and J. Ville "Thovrie et applications de la notion de signal analylique", Cables et Transmission, vol. 2, pp. 61–74 (1948).

The Wigner-Ville transform, defined mathematically as:

$$W_x(t,f) = \int x(t+\tau/2)x^*(t-\tau/2)e^{-j2\pi f\tau}d\tau$$

satisfies a number of desirable mathematical properties and possesses optimal resolution in time-frequency space. Application of the Wigner-Ville transform allows more subtle signal features to be detected, such as those having short length and high frequency variation.

Heretofore, the use of the Wigner-Ville transform has been limited because of the presence of cross or interference terms. The Wigner-Ville transform of the sum of two signals x(t)+y(t)

$$W_{x+y}(t,f) = W_x(t,f) + 2\Re(W_{xy}(t,f)) + W_y(t,f)$$

has a cross term $2\Re(W_{xy}(t,f))$ in addition to the two auto components $W_x(t,f))$ and $W_y(t,f))$. The cross terms of the Wigner-Ville transform are due to the WVD's quadratic structure. They occur in the case of multicomponent signals and can be represented mathematically with quadratic cross terms. Because the cross term usually oscillates and its magnitude is twice as large as that of the auto components it can interfere with the useful time dependent spectral patterns.

Accordingly, if the transform produces interference terms, these interference terms should be minimized for appropriate interpretation and discrimination of the signals being analyzed. This step is indicated by the reference numeral 35 in FIG. 5. While filtering of the interference terms is desirable, the use of linear filters can distort the resolution and concentration of the auto component terms. A non-linear filter is therefore used. The "center affine filter" as described by G. R. Arce and S. R. Hasan, "Elimination of interference terms of the discrete wigner transform using nonlinear filtering," *IEEE Transactions on Signal Processing*, vol. 48, August 2000 is preferred. The center affine filter can be applied to effectively filter the cross terms while leaving the auto component terms relatively unaffected.

The next step in the method, indicated by the reference numeral 40 in FIG. 5, is the identification of clusters of data having a common frequency characteristic in the time-frequency domain, thereby to identify proteins of a common functional family. This step may be accomplished in several ways.

The clusters may be identified using any of the well-known cluster identification algorithms, such as a minimum distance classifier. Alternatively, the resulting transformed data may be visually rendered by a plot in the time-frequency domain and the clusters may be manually identified.

An amplitude analysis of the clusters of data points may reveal information about biological activity. So called "hot spots", i.e., data points whose amplitude exceeds a predetermined threshold, may identify biologically active regions in the protein.

The method is preferably practiced by a digital computer operating under any common operating system, such a Windows-based operating system (Microsoft Corporation, Redmond, Wash.), a Unix-based operating system, or Linux-based operating system, using an integrated mathematics package such as MATLAB from MathWorks, and callable routines written in the C programming language.

The advantages of the method of the present invention may be appreciated from its application to the Fibroblast Growth Factors as used in the experiments described by Fang and Cosic previously described as well as a homeodomain Proteins example to be developed.

EXAMPLE 1

Fibroblast Growth Factors

The experiments described by Fang and Cosic have shown that the potential cell attachment sites of FGF's are between residues 46–48 and residues 88–90 and the characteristic frequency has been shown in the literature as 0.4512.

Figure 6:
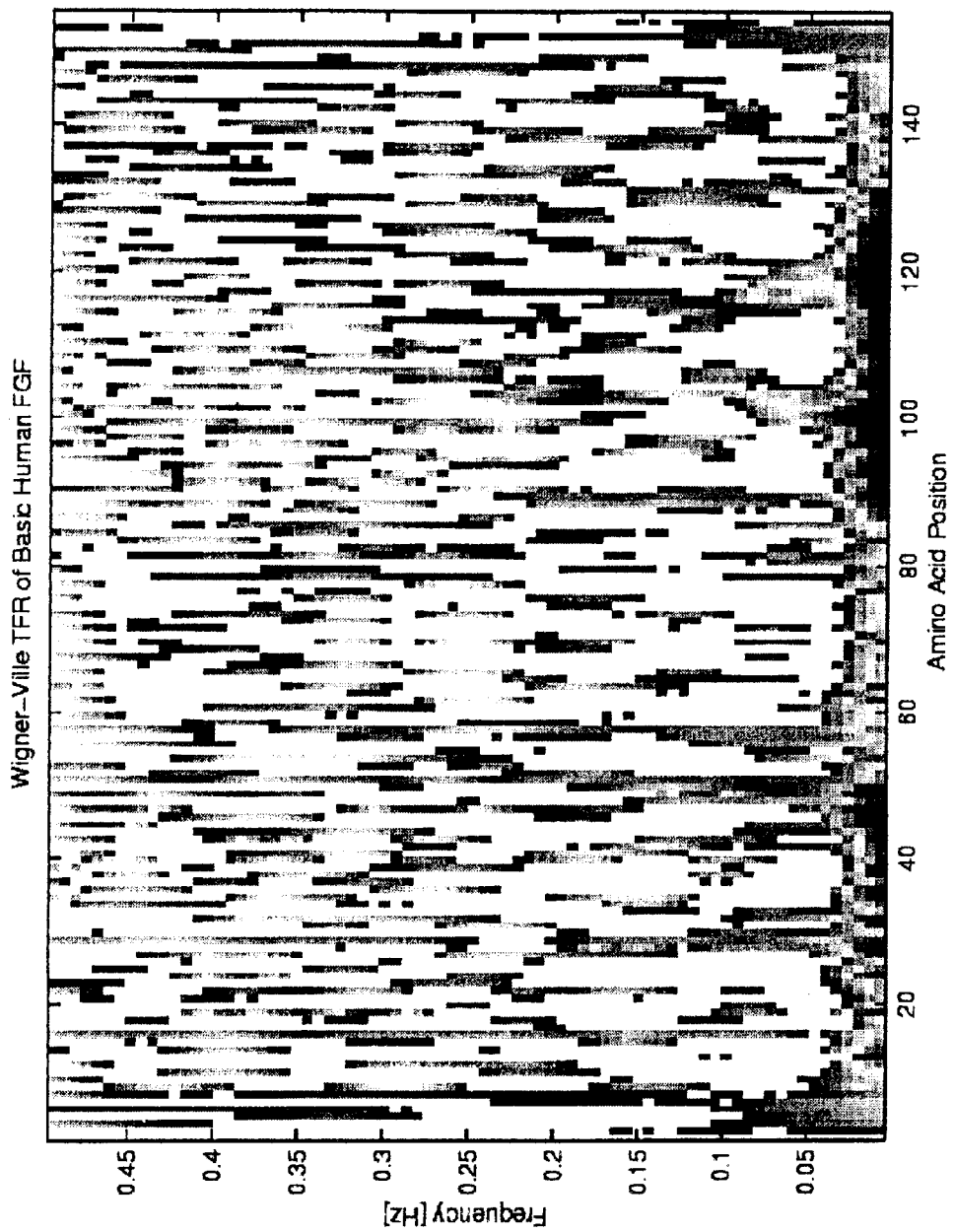
FIG. 6 shows a gray scale intensity plot of a Wigner-Ville time-frequency representation of basic FGF human of Example 1.
Figure 7:
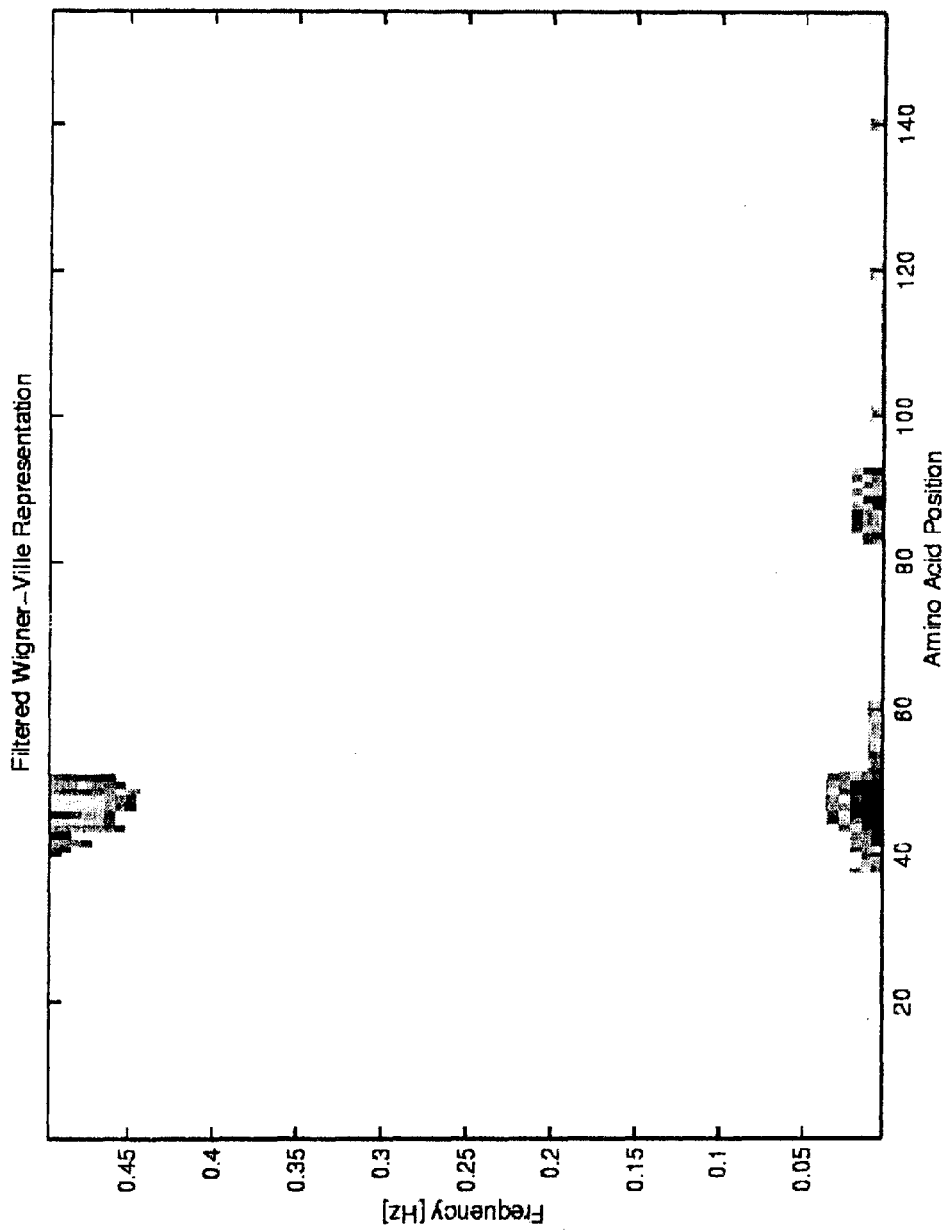
FIG. 7 is a gray scale intensity plot that shows activation sites of fibroblast growth factor of Example 1.

The discrete Wigner-Ville time-frequency representation of human basic FGF and EIIP representation is shown in FIG. 6 as a gray scale intensity plot. After elimination of the cross terms by the application of the center affine filter as described by Arce and Hasan, the bright regions (i.e., light gray) seen in the gray scale intensity plot of FIG. 7 are clusters which have a common characteristic frequency component corresponding to proteins of a common functional family. It should be noted that the amplitude represented by the bright regions in fact correspond to experimentally proven biologically active regions in the protein.

EXAMPLE 2

Homeodomain Proteins

Homeodomain proteins contain a sixty amino acid DNA binding domains found in numerous eukaryotic transcription factors. The homeodomain family is a useful system for studying sequence-structure and sequence-function relationships because several hundred sequences are known and the structures of several homeodomains have been determined and are discussed by N. D. Clarke in "Covariation of residues in the homeodomain sequence family," *Protein Science*, vol. 4, November 1995.

Figure 8:
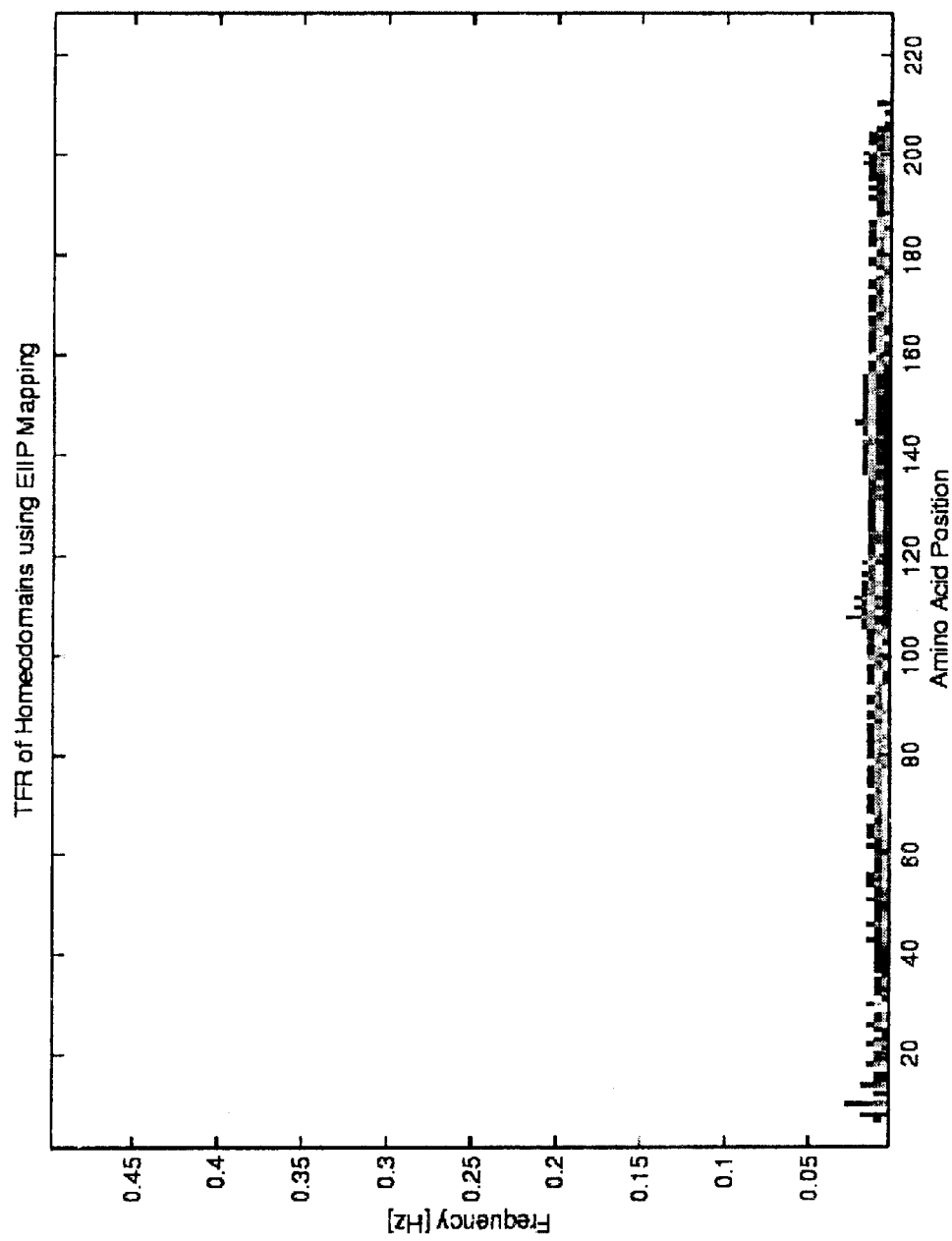
FIG. 8 is a gray scale intensity plot of a time-frequency response of homeodomain proteins of Example 2 using the EIIP mapping.
Figure 9:
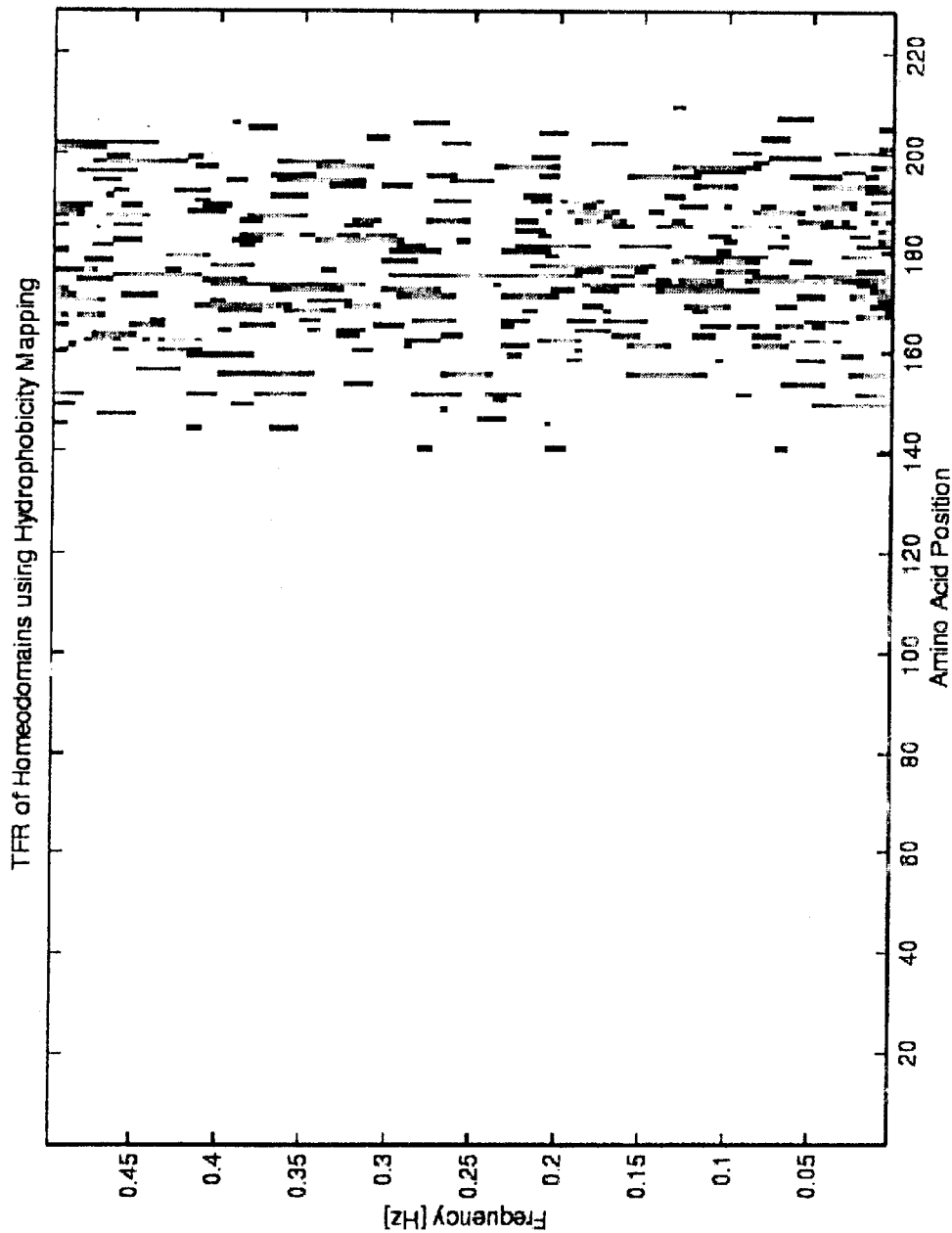
FIG. 9 is a gray scale intensity plot of a time-frequency response of homeodomain proteins of Example 2 using a hydrophobicity mapping.

Application of the Wigner-Ville time-frequency representation to a homeodomain B6 protein that has been represented via the EIIP mapping results in the gray scale intensity plot shown in FIG. 8. There doesn't appear to be any clear signature in the plot which one could relate to active regions on the protein. However, if an alternative mapping is used, such as one measuring the hydrophobicity of the amino acids as illustrated in the gray scale intensity plot of FIG. 9, a clear indication of the homeodomain is detected. The binding domain is located at amino acid positions 146–205. This example illustrates the importance of the particular numerical representation being used to describe the protein family being studied.

Discussion As illustrated by Examples 1 and 2 the present method illustrates the usefulness of time-frequency signal processing for the analysis of protein sequence data, and thus for the analysis of data representing a biological element. Time-frequency representations such as the Wigner-Ville transform, when appropriately filtered for interference terms, can provide frequency as well as spatial information leading to the identification of biologically active sites of certain proteins and in general biologically active regions of certain biological elements. However, as illustrated in the homeodomain Example 2, the selection of the numerical mapping is problem specific since different mappings will highlight different structural properties of the proteins which are directly related to a protein's function. More generally stated, different mappings will highlight different structural properties of the biological elements which are directly related to that element's function. The use of multiple numerical representations of the amino acids provides a multidimensional representation of physico-chemical measurements at each amino acid position. The well-known clustering algorithms, cited above, are capable of analysis of these multidimensional representations.

GenomeNet, a Japanese network of database and computational services for genome research, which may be found on the "GenomeNet WWW Server" of the Institute for Chemical Research, Kyoto University at website http://www.genome.ad.jp/dbget/aaindex.html, currently maintains a database of over four hundred different numerical mappings of amino acids. This is further described by S. Kawashima, H. Ogata, and M. Kanehisa in "Aaindex: Amino acid index database," *Nucleic Acids Research*, volume 27, January 1999. The ability to correlate these indices and select a subset for use as a multidimensional representation of data at each amino acid location is an extension of the present method. The ability to have vector data at each amino acid location reflecting various physico-chemical properties simultaneously has the potential to strengthen time-frequency analysis approach described in this application.

Prior art analysis methods for gene expression typically rely on detecting relationships between genes with a significant linear component. However, the assumption of a Gaussian distribution of the gene expression values is not always valid.

The present invention can also be used in the context of classifying a gene (the biological element) into a functional family from a set of gene expression values (the biological subelements) by the use of a combination of linear and nonlinear correlation methods.

After gene expression values for a set of genes which represent a characteristic (i.e., an amount of expression) relative to a control for the individual genes as a function of time and/or experimental condition is acquired, the method of classifying a gene in an organism into a functional family comprises the following steps:

If there is a time or spatial relationship between the components of the gene expression values, transforming each gene expression value into a time-frequency domain, as by using a wavelet transform or a Wigner-Ville transform;

Separating the time-frequency representation of the gene expression values into linear and non-linear components, as by affine filtering;

Correlating the linear and non-linear components of the gene expression values in a pair-wise manner. This is done by computing a linear correlation measurement (such as the well-known Pearson correlation) on the linear components and a non-linear correlation measurement (such as a median correlation) on the nonlinear components. If the time-frequency transform was not performed, the linear and nonlinear correlations of the gene expression values are computed on the original gene expression values;

Using the linear and nonlinear correlations for each gene pair, cluster the gene expression values using a clustering method such as hierarchical clustering, thereby to identify clusters of similar genes and thereby classify a gene in an organism into a functional family.

Figure 10:
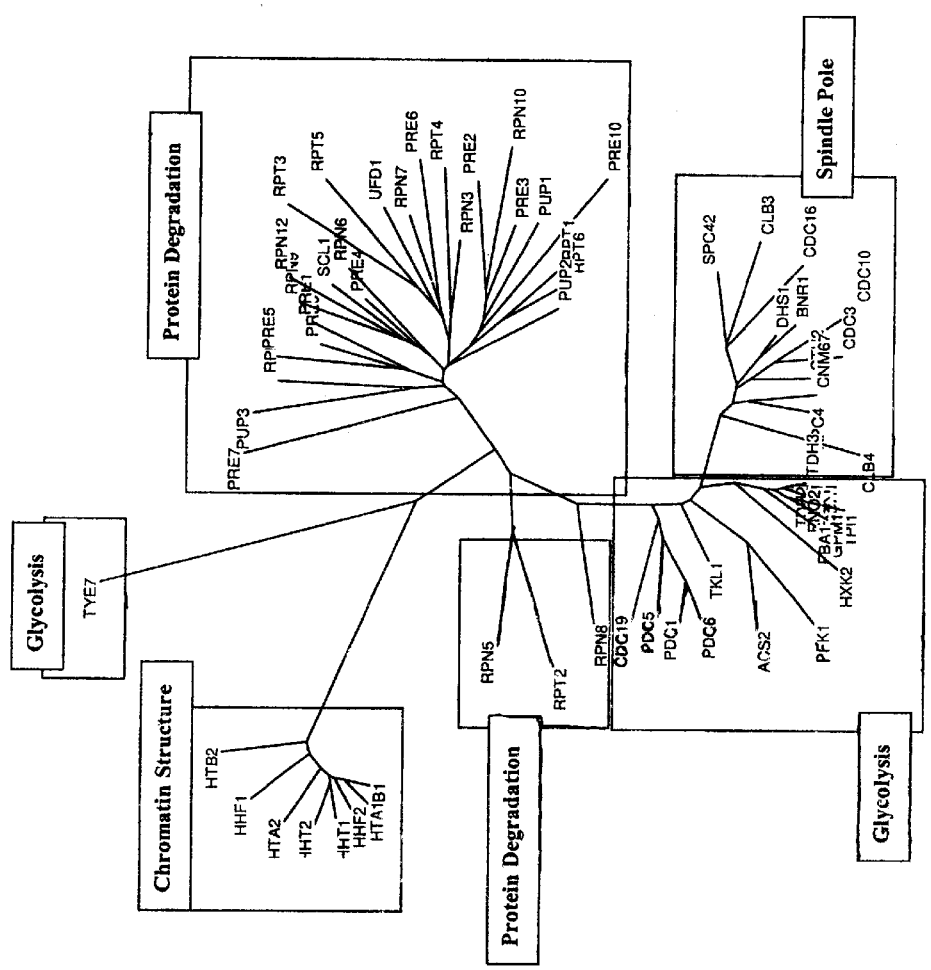
FIG. 10 shows results from a prior art hierarchical clustering algorithm using a linear correlation to visualize relationships amongst genes.

Example 3 The same subset of yeast data as was used in the Eisen experiment discussed in conjunction of FIG. 10 was employed as an example to illustrate the use of the present invention.

Figure 11:
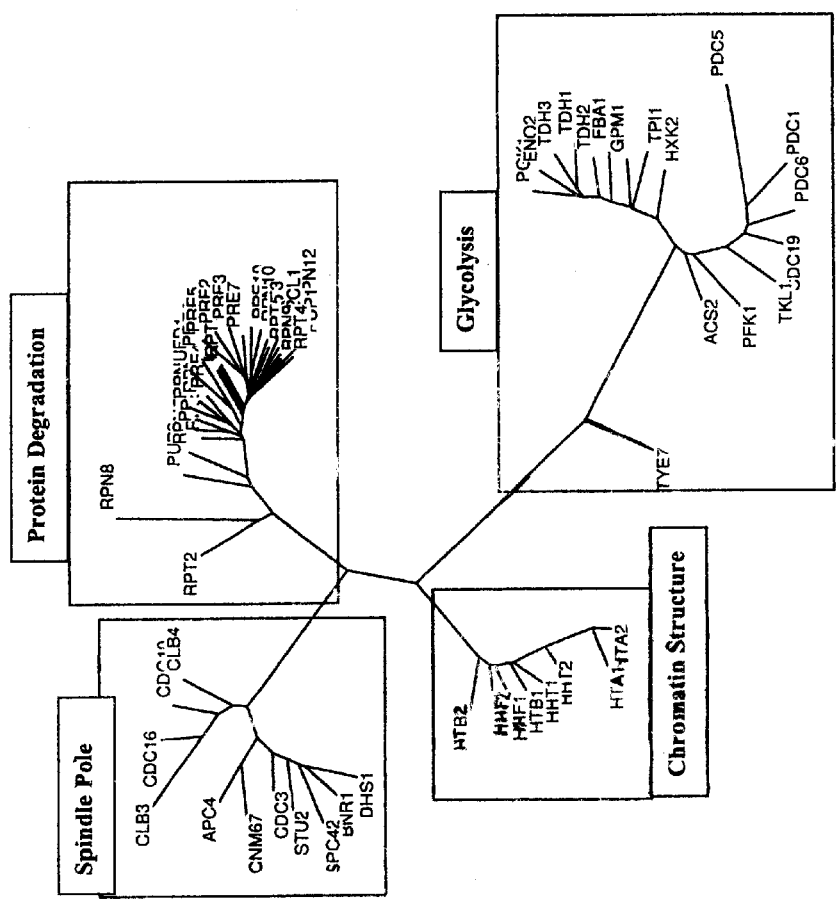
FIG. 11 shows relationships among genes, using the nonlinear correlation of the present method, with a hierarchical clustering algorithm.

Using the present invention, both the linear correlation metric and a nonlinear median correlation coefficient were computed. This information was then passed to a clustering method such as hierarchical clustering. The result is shown in FIG. 11. The data in this example is known to be classified into four functional classes: "spindle pole", "glycolysis", "protein degradation" and "chromatin structure". From a comparison of FIGS. 10 and 11 it can readily be seen that the clustering provided by the present invention improves the classification of the genes into their functional families.

In summary, in view of the foregoing, it may be appreciated that the present invention provides a analysis methodology for the classification of a biological element into a functional family and a methodology for identification of biologically active regions of the biological element.

Having benefit of the above description one skilled in the art will appreciate that the present invention may be extended to situations where multiple sets of characteristic values representative of multiple properties of a biological subelement are available. It should also be understood other filtering techniques may be used to remove the interference terms from the transformed data.

What is claimed is:

1. A method of classifying a biological element comprised of biological subelements into a functional family, wherein each family is represented by a cluster of data points around a common frequency characteristic of a time-frequency transform, the method comprising the steps of:

a) converting a symbolic representation of a sequence of biological subelements of the biological element to a numeric representation of that sequence;

b) performing a time-frequency transform on the numeric representation;

c) identifying a cluster of data having a common frequency characteristic in the time-frequency domain, thereby to identify the biological element in the functional family corresponding to that cluster of data points.

2. The method of claim 1 further comprising, after step b), the step of:

b1) filtering interference terms from the transformed data.

3. The method of claim 2 wherein, the time-frequency transform is the Wigner-Ville time-frequency transform.

4. The method of claim 3 wherein, the interference terms of the Wigner-Ville time-frequency transform are filtered using the center affine filter method.

5. The method of claim 1 wherein the numeric representation is a scalar representation of a functional characteristic of each biological subelement of the biological element.

6. The method of claim 1 wherein the numeric representation is a vector representation of multiple functional characteristics of each subelement of the biological element.

7. The method of claim 6, wherein the vector representation is reduced to a minimal set of dimensions which preserves the functionally important characteristics of one or more subelements of the biological element.

8. The method of claim 1, further comprising the step of:

d) identifying clusters of data points whose amplitude exceeds a predetermined threshold, thereby to identify biologically active regions in the biological element.

9. The method of claim 1, further comprising the step of:

d) repeating steps a) through c) for a second biological element, and e) identifying clusters of data points whose amplitude exceeds a predetermined threshold, thereby to identify relationships among the first and second biological elements.

10. The method of claim 1 further comprising the step of:

after step b), plotting the resulting transformed data in the time-frequency domain to create a visual representation of the transformed data.

11. A method of classifying proteins into functional families comprising the steps of:

a) converting a symbolic representation of a primary amino acid sequence data to a numeric representation of that sequence;

b) performing a time-frequency transform on the numeric representation;

c) identifying clusters of data having a common frequency characteristic in the time-frequency domain, thereby to identify proteins of a common functional family.

12. The method of claim 11 wherein the numeric representation is a scalar representation of a physico-chemical property of each amino acid of the primary amino acid sequence data.

13. The method of claim 11, wherein the numeric representation is a vector representation of multiple physico-chemical properties.

14. The method of claim 13, wherein the vector representation is reduced to a minimal set of dimensions which preserves the functionally important features of the protein.

15. The method of claim 11, further comprising the step of:
- d) identifying clusters of data points whose amplitude exceeds a predetermined threshold, thereby to identify biologically active regions in the protein.

16. A method of classifying a gene in an organism into a functional family from a set of expression data for a set of genes, the data representing, relative to a control, a characteristic for each individual gene as a function of experimental condition, comprising the steps of:
- a) converting the gene characteristic to a numeric representation of that characteristic;
- b) identifying linear components and nonlinear components of the genes; and
- c) performing a linear correlation on the linear components and a nonlinear correlation on the linear components to identify clusters of data having a common frequency characteristic in the time-frequency domain;

thereby to identify the gene as a member of a functional family.

17. The method of claim 16, where the data representing a characteristic for each individual gene is time-varying, further comprising, after step a), the step of:
- a1) performing a time-frequency transform on the numeric representation of the gene characteristic.

* * * * *

SEQUENCE LISTING

<160> NUMBER OF SEQ ID NOS: 2

<210> SEQ ID NO 1
<211> LENGTH: 146
<212> TYPE: PRT
<213> ORGANISM: Bos Taurus

<400> SEQUENCE: 1

```
Pro Ala Leu Pro Glu Asp Gly Gly Ser Gly Ala Phe Pro Pro Gly His
 1               5                  10                  15

Phe Lys Asp Pro Lys Arg Leu Tyr Cys Lys Asn Gly Gly Phe Phe
            20                  25                  30

Leu Arg Ile His Pro Asp Gly Arg Val Asp Gly Val Arg Glu Lys Ser
                35                  40                  45

Asp Pro His Ile Lys Leu Gln Leu Gln Ala Glu Glu Arg Gly Val Val
        50                  55                  60

Ser Ile Lys Gly Val Cys Ala Asn Arg Tyr Leu Ala Met Lys Glu Asp
    65                  70                  75

Gly Arg Leu Leu Ala Ser Lys Cys Val Thr Asp Glu Cys Phe Phe Phe
80                  85                  90                  95

Glu Arg Leu Glu Ser Asn Asn Tyr Asn Thr Tyr Arg Ser Arg Lys Tyr
                100                 105                 110

Ser Ser Trp Tyr Val Ala Leu Lys Arg Thr Gly Gln Tyr Lys Leu Gly
            115                 120                 125

Pro Lys Thr Gly Pro Gly Gln Lys Ala Ile Leu Phe Leu Pro Met Ser
        130                 135                 140

Ala Lys Ser
    145
```

```
<210> SEQ ID NO 2
<211> LENGTH: 140
<212> TYPE: PRT
<213> ORGANISM: ACID TAURUS

<400> SEQUENCE: 2

Phe Asn Leu Pro Leu Gly Asn Tyr Lys Lys Pro Lys Leu Leu Tyr Cys
1               5                   10                  15

Ser Asn Gly Gly Tyr Phe Leu Arg Ile Leu Pro Asp Gly Thr Val Asp
            20                  25                  30

Gly Thr Lys Asp Arg Ser Asp Gln His Ile Gln Leu Gln Leu Cys Ala
        35                  40                  45

Glu Ser Ile Gly Glu Val Tyr Ile Lys Ser Thr Glu Thr Gly Gln Phe
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys His Trp Phe Val Gly Leu Lys
            100                 105                 110

Lys Asn Gly Arg Ser Lys Leu Gly Pro Arg Thr His Phe Gly Gln Lys
        115                 120                 125

Ala Ile Leu Phe Leu Pro Leu Pro Val Ser Ser Asp
    130                 135                 140
```